United States Patent [19]
Ono et al.

[11] 4,326,801
[45] Apr. 27, 1982

[54] METHOD FOR EMISSION SPECTROCHEMICAL ANALYSIS

[75] Inventors: Junichi Ono; Isao Fukui; Naoki Imamura, all of Kyoto, Japan

[73] Assignee: Shimadzu Seisakusho, Ltd., Kyoto, Japan

[21] Appl. No.: 163,163

[22] Filed: Jun. 26, 1980

Related U.S. Application Data

[63] Continuation-in-part of Ser. No. 862,124, Dec. 12, 1977, abandoned.

[30] Foreign Application Priority Data

Dec. 20, 1976 [JP] Japan ................................. 51-153815

[51] Int. Cl.³ ........................................... G01N 21/66
[52] U.S. Cl. .................................................. 356/313
[58] Field of Search ................................ 356/313, 314

[56] References Cited
U.S. PATENT DOCUMENTS 3,876,306 4/1975 Onodera et al. ..................... 356/313

*Primary Examiner*—Vincent P. McGraw
*Attorney, Agent, or Firm*—Armstrong, Nikaido, Marmelstein & Kubovcik

[57] ABSTRACT

A method of emission spectrochemical analysis is provided which comprises the steps of producing a predetermined number of spark discharges between an electrode and a specimen containing an element in a first and second state. The intensity of emission of light caused by each of the spark discharges is measured and a frequency distribution of the measured intensities of emission is obtained. The distribution is separated into an area of normal distribution and an area outside the area of normal distribution, and an intensity of emission value is selected. The amount of the element in the first state is determined as a function of the selected intensity of emission multiplied by the area of normal distribution and the amount of the element in the second state is determined as a function of the selected intensity of emission multiplied by the area outside the area of normal distribution.

4 Claims, 7 Drawing Figures

METHOD FOR EMISSION SPECTROCHEMICAL ANALYSIS

RELATED APPLICATION

This application is a continuation-in-part of application Ser. No. 862,124, issued Jan. 12, 1977 now abandoned.

BACKGROUND OF THE INVENTION

This invention relates to a method of emission spectrochemical analysis which can determine the quantitative analysis of other elements in a metal.

In metallurgy, such a measurement is usually taken to determined a specified element which has been added into a metal for the purpose of improving some property the metal, degassing, purifying, or arranging the particle size of crystals of the metal, etc. In the case of steel, for example, aluminum is added to steel for the purpose of turning the steel into a non-aging steel through removing the oxygen in the steel or stabilizing the nitrogen in the steel. It results in that the steel includes a hemogeneous type of Al mixed with steel uniformly into an alloy and a heterogenous type of Al as scattering in the texture of steel in the form of aluminum oxide ($Al_2O_3$).

As for the latter, the aluminum oxide scattering in the form of heterogeneity is generally not a favorable constituent of steel and specifically larger particle sizes of aluminum oxide or scattered groups thereof deteriorate the mechanical properties of the steel.

The properties of steel vary depending on the ratio of the homogeneity to the heterogeneity even if the total quantity of Al in the steel is the same. It is necessary, therefore, to control the ratio of homogenious to heterogenous Al as well as the total quantity of Al in steel, and thus, this kind of quantitative analysis is required.

The quantitative measurement by the emission spectrochemical analysis can be made more speedily performed than by means of chemical analysis and it is possible to allow favorable treatment in the quality control or process control of steel by controlling the required quantity of Al to be added to steel. Thus, the method of analysis mentioned above has been adopted to determine the total quantity of mixed elements and their existing state.

Emission spectrochemical analysis can determine the quantitative analysis of mixed elements in a specified metal as well as their existing state on the basis of the principle that a sample produces an emission with spark discharging. The specified elements are detected through the spectrochemical analaysis wherein although the intensity of emission varies in each emission, strong intensity of emission is seen many times in the first stage of the repetition of spark discharging and then as time passes the accompanying strong intensity of emission is decreased and the variation of the intensity of emission becomes less. The difference between the mean of each intensity of emission seen in the first stage and that of those seen in the stabilized or later stage relates to the ratio of the homogeneity to heterogeneity.

The phenomenon mentioned above exhibits a large intensity of emission when a spark discharging arises between the electrode and the element mixed in a sample in a heterogeneous condition and thereafter the heterogeneous matter will not emit so strongly even when subjected to a spark discharging on account of vaporization, dispersion with fine differentiation, etc,. However, it is hard to make an accurate analysis in this case as even homogeneous elements exhibit the tendency of the dropping of intensity of emission as the spark discharging is repeated.

A method of quantatitive analysis is shown in U.S. Pat. No. 3,876,306 wherein the light volume of the specified element including its homogeneous state and its heterogeneous state is obtained through the spark discharging between a sample and an electrode. The light volume is converted into a current of light, the total photoelectric current of the element is integrated, the value of the photoelectric current of the homogeneous state is integrated on the basis of the mean of the photoelectric current of the homogeneous state among those products of the specified element mentioned above, the difference between the former integrated value and the latter integrated value is calculated, and thus the content of said specified element in the sample in its homogeneous state and its heterogeneous state are separately determined. This method is not, however, satisfactory from the viewpoint of its evaluation in accuracy, etc.

Although the analyzing method mentioned above can be carryied out in less time in comparison to chemical analysis, it still takes several tens of seconds of time and the reproductivity of its measured result and the accuracy of analysis are not good. This is due to the fact that the variation of the intensity of emission through the spark discharging is not stable and the same result is hard to obtain even with the same sample.

SUMMARY OF THE INVENTION

The purpose of this invention, therefore, is to provide an emission spectrochemical analysis method capable of feasibility in a short time, solving the problems of the conventional methods, and having good reproducability with high accuracy of analysis.

BRIEF DESCRIPTION OF THE DRAWINGS

FIG. 1 and FIG. 2 show the histogram of the frequency distribution of the intensity of emission in an emission spectrochemical analysis method wherein FIG. 1 is the histogram of frequency distribution where the specified element exists in a metal in a state of homogeneity and FIG. 2 is the histogram where the element exists in a metal in the mixed state of homogeneity and heterogeneity;

DETAILED DESCRIPTION OF THE PREFERRED EMBODIMENT

Figure 1:
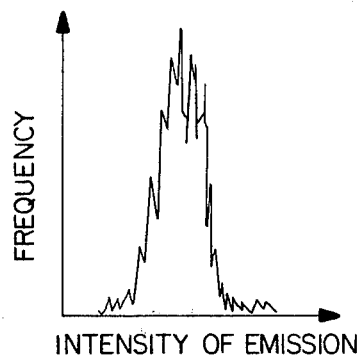
Figure 2:
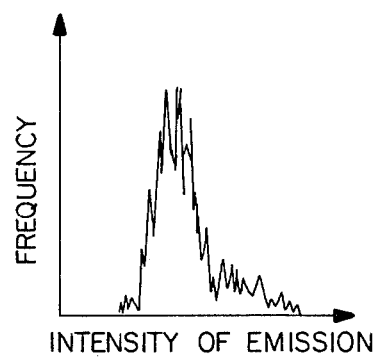

If spark discharging is repeated several times with a sample and an emission spectrochemical analysis of the emission is made in each spark discharging, with a histogram of the frequency distribution of the intensity of each emission of the element being made, the histogram of the frequency distribution shows an approximate normal distribution as shown in FIG. 1 when the element exists in the state of homogeneity. On the other hand, when the histogram shows such a distribution deviating much from a normal distribution as shown in FIG. 2, the element exists in a mixed state of homogeneity and heterogeneity. The distribution which is formed in this case is one-sided towards the side of larger intensity of emission. In this case, therefore, it can be said that the area of the curve of frequency distribution outside of the area of normal distribution shows the ratio of the quantity of heterogeneity to that of homogeneity of the specified element included in a metal.

This invention has been conceived on the basis of the idea mentioned above wherein it is not required to repeat spark discharging until the intensity of emission has been stabilized. This technique can save analyzing time and thus allows less analyzing time as compared with the conventional analyzing methods. Furthermore, the technique of the present invention makes a more accurate analysis with higher reproducability because it takes the form of the frequency distribution into account, with little emphasis on the intensity of emission itself.

Figure 3:
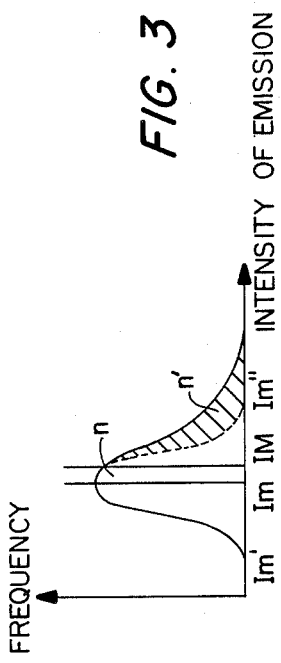
FIG. 3 is a simplified frequency distribution explaining the analysis method relating to the present invention.

FIG. 3 is a simplified curve of the distribution of frequency of the intensity of emission.

When an element to be detected exists in both the state of homogeneity and that of heterogeneity, a curve expressing the frequency distribution of the intensity of emission has a long trailing edge on the higher side of the intensity of emission since a higher intensity of emission results from the element in the state of heterogeneity. The peak of the curve in FIG. 3 is considered as the Mode value Im of the frequency distribution of the intenity of emission caused by the element in the homogeneous state. If the area below the curve between the Mode value Im and the starting point Im' of the curve on that side of the center where the intensity of emission is relatively low is doubled symmetrically, the resulting area wil be considered as that of the normal frequency distribution of the intensity of emission caused by the element in the homogeneous state. Therefore, if the cumulative frequency in the former half area is doubled, the frequency "n", or number of emissions, of the intensity of emission caused by the element in the homogeneous state is obtained. Then, the frequency n thus obtained is subtracted from the total freqency N; that is, the predetermined total number of times of emission so as to obtain a frequency n'. Then the median value IM of the total intensity of emission is multiplied by each of the frequencies n and n' to obtain a measured value for the element in each of the homogeneous and heterogeneous states. By applying the measured values to a calibration curve previously plotted by a known sample, it is possible to quantitatively determine the element under measurement in each of the two states.

In case of processng the procedure mentioned above with FIG. 1 and FIG. 2, the position Im showing the maximum frequency and the leading edge of the distribution curve are somewhat hard to be set because of the roughness of the histograms. In this case, therefore, the following substitutive method may be taken:

As the total number of spark discharges are previously known, the area under the curve referring to FIG. 3 is to be integrated, startng at the leading edge, which is usually positioned on the side of less intensity of emission in such a way that the intensity of emission where the integrated area reaches 1% of the total area is the point Im' and, further, the intensity of emission where the integrated area reaches 30% of the total area is Im. In this case, the value 30% is not required and the value of percentage may be selected according to the conditions of an individual case adopting this method, In other words, the value 30% is an approximate standard value.

The method mentioned above is avilable in particular when the amount of a specified element in the latter existing state is less than that of the element in the former existing state. The method, therefore, is available specifically for making the quantitative analysis of the elements included in steel, such as A (aluminum), B (boron), Ti (Titanium) and S (sulfur), etc.

Figure 5:
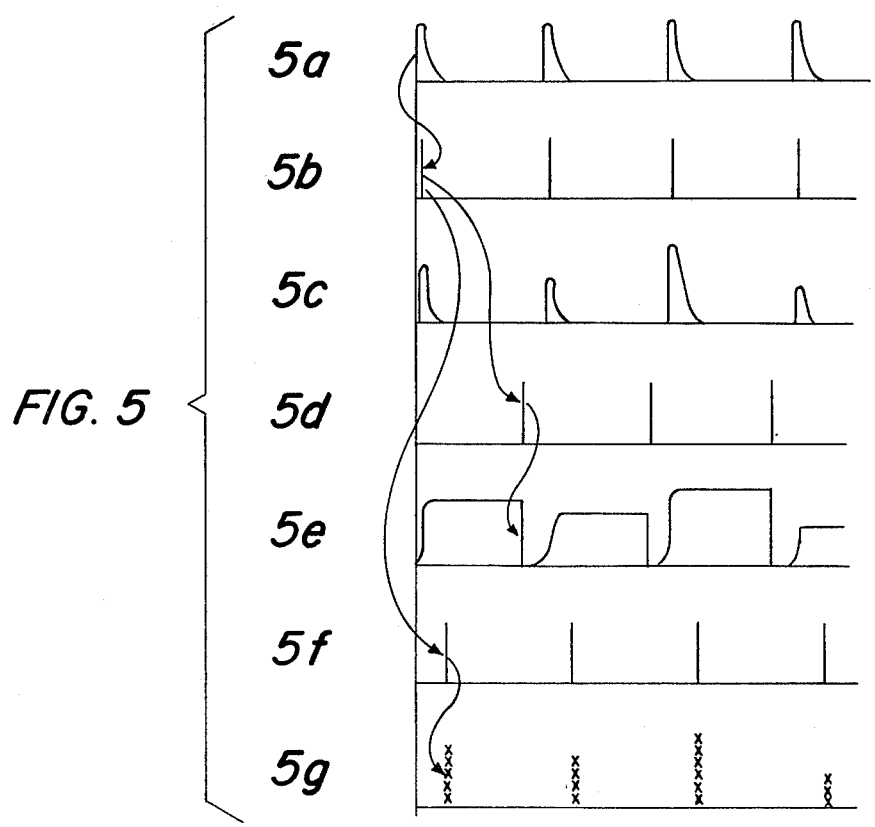
FIGS. 5a–5g are waveforms at various points in the circuit of FIG. 4.
Figure 4:
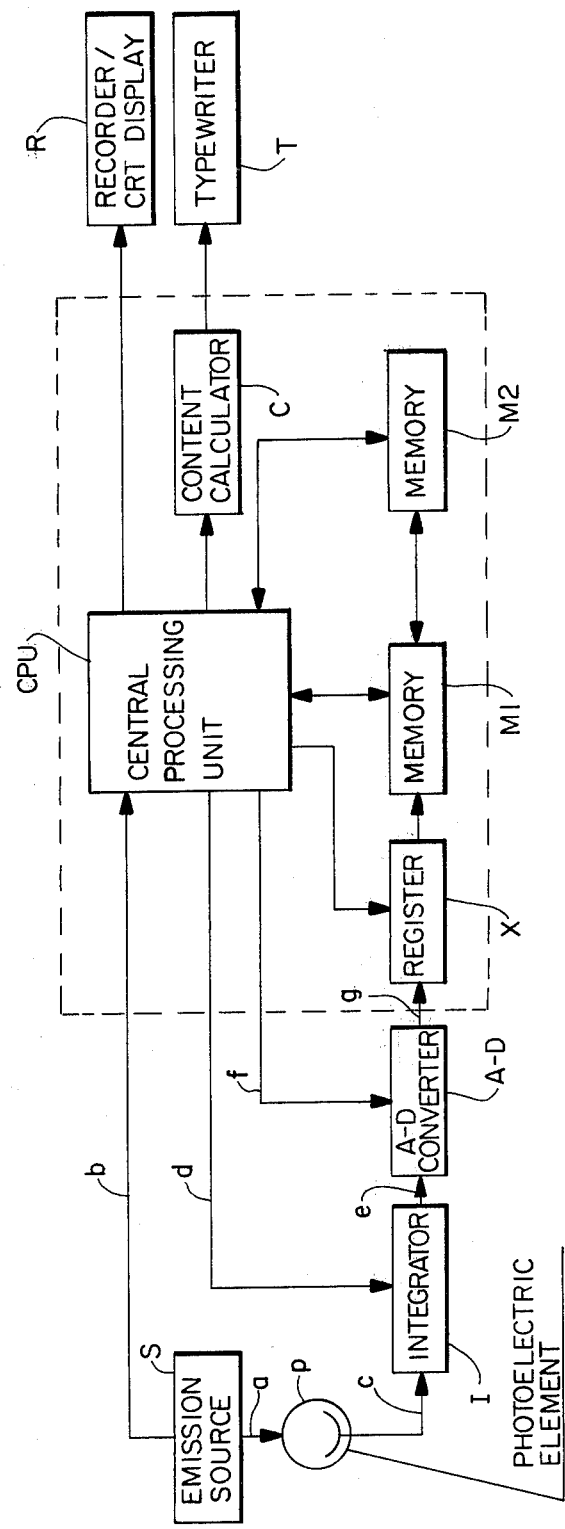
FIG. 4 is a block diagram of an apparatus for carrying out the method of the present invention.
Figure 6:
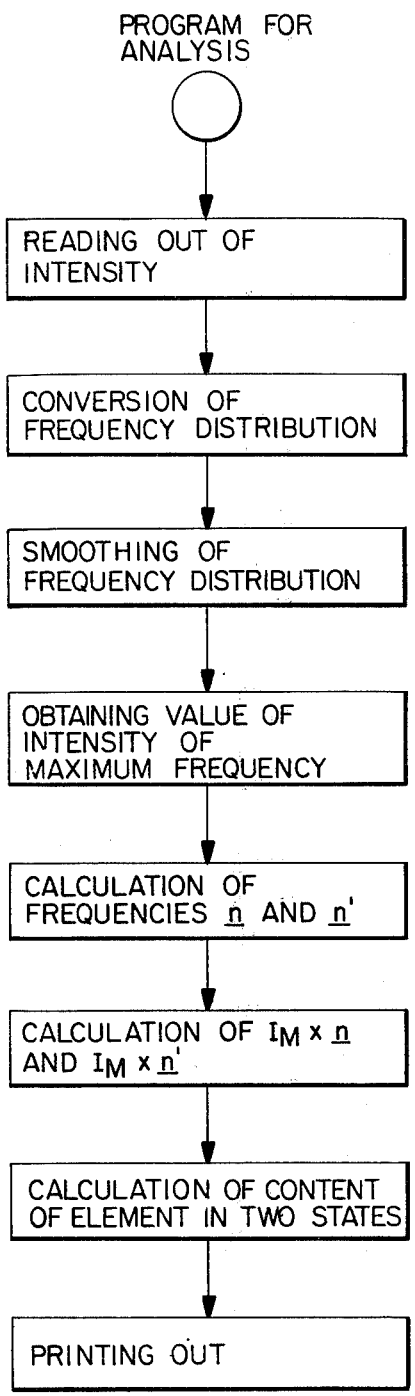
FIG. 6 is a program for carrying out the method of the present invention.
Figure 7:
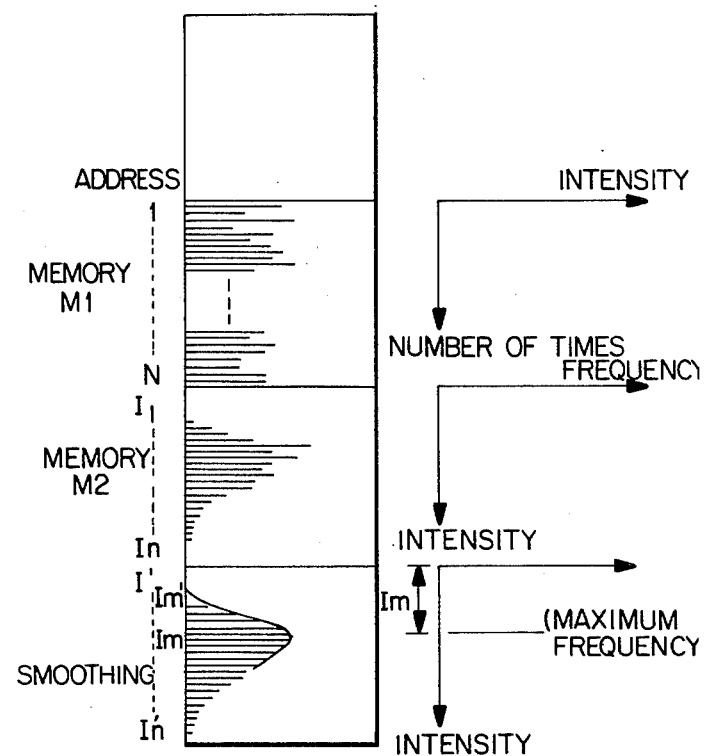
FIG. 7 is a timing chart of the method of the present invention.

FIG. 4 is a block diagram of an apparatus suitable for carrying out the method of the present invention and FIGS. 5a–5g are the waveforms of the signals produced by the various components of the apparatus. FIG. 6 shows a program for performing the analysis, together with a timing chart shown in FIG. 7, wherein the program area on the central processing unit CPU, the functions of the memories M1 and M2 and the operation of smoothing the data in the memory M2 are shown. The operations for obtaining the measured values of the element in such of the states is also illustrated.

Referring first to FIG. 4, in the source of emission S, a spark current causes a spark discharge to repeatedly occur between a specimen (not shown) to be tested and an electrode (not shown) opposite the specimen. The light a emitted at each discharge is detected by a photoelectric element P, the output c of which is applied to a single-pulse integrator I. An analog-digital converter A-d receives the output analog signal e produced by the integrator I and converts it to a digital signal g. A register X, which is reset synchronously with the emission of light by the source S immediately before the emission, temporarily stores the output g of the converter A-D. The source S also produces a synchronizing signal b in synchronism with the previously mentioned spark current. In response to the signal b, a central processing unit CPU produces a discharge signal d and a start signal f to control the operations of the integrator I and the A-D converter A-D, respectively.

The central processing unit CPU also causes the memory M1 to memorize the contents of the register X each time the source S emits light. As illustrated in FIG. 5, the CPU counts the number of times of emission of light and gives the designation No. 1 through No. N, corresponding to the counted values to the addresses in the memory M1. The intensity of light at each of the emissions is stored successively in the addresses No. 1 through No. N in the memory M1.

When a predetermined number of emissions have occurred, the CPU reads out the values stored in the addresses of the memory M1 sequentially and puts the read-out data into the memory M2 to be stored therein. In the memory M2, the addresses are numbered 1' through N', each corresponding to one of the different values of the intensity of emission which are stored in the addresses of fhe memory M1.

The memories read out by the CPU from different addresses in the memory M1 may often have the same value of the intensity of emission and these memories of the same value are successively stored in the same address in the memory M2 corresponding to that intensity of emission. In other words, each time the memory of the same intensity of emission is read out from the memory M1, one (1) is added to the memory existing in the same address in the memory M2 corresponding to the intensity of emission.

In this manner, when the CPU has read out all the data in the memory M1 and put it into the memory M2, the storage in the memory M2 expresses the frequency distribution of the intensities of emission caused by the element under measurement at the predetermined number of discharges. The data in the memory M2 may be read out for display and/or recording of the frequency distribution in a CRT display and/or a recorder R.

For accurate determination of the intensity value of the maximum frequency, the frequency distribution in the memory M2 is smoothed.

To obtain the frequency n of the emission caused by the element in the homogeneous state, the smoothed data is read out successively from the starting point Im' of the distribution curve to the point Im where the frequency of the intensity is maximum, and the read-out data is summed to produce the cumulative frequency up to the intensity Im, which is the frequency in half the area of the normal distribution. Then the cumulative frequency is doubled to obtain the frequency n of the intensities of emission caused by the element in the homogeneous state.

Since the number of times N of emission is predetermined, subtraction of n from N will give the frequency n' of the emission caused by the element in the heterogeneous state (N−n=n'). Then the value of the average intensity (that is, the median value IM) is obtained from the frequency distribution of the intensity of emission stored in the memory M2. By multiplying each of the frequencies n and n' by the value IM, it is possible to obtain the measured values for the element in each of the two states.

Each of the measured values is applied to a content calculator C, which gives the content of the element in each of the states in the specimen. The contents are printed out by a typewriter T.

The embodiment of this invention mentioned above is only an example of the analyzing procedure with a computer. Therefore, it is possible to make many other ways computation if making use of the storages of memory M1 and M2.

For the reference, the test results of the quantitative analysis of A mixed in steel of its existing states, such as homogeneous one and heterogeneous one, through the chemical analysis, the conventional method, and the method relating to this invention, are as follows:

| Sample No. | Kind of mixing state | Content through chemical analysis (%) | Content through conven. method(%) | Content through this invention(%) |
|---|---|---|---|---|
| 1 | Homogeneous | 0.002 | 0.015 | 0.002 |
|   | Heterogeneous | 0.032 | 0.021 | 0.030 |
| 2 | Homogeneous | 0.018 | 0.023 | 0.018 |
|   | Heterogeneous | 0.008 | 0.005 | 0.008 |
| 3 | Homogeneous | 0.032 | 0.043 | 0.033 |
|   | Heterogeneous | 0.018 | 0.006 | 0.019 |
| 4 | Homogeneous | 0.042 | 0.053 | 0.041 |
|   | Heterogeneous | 0.006 | 0.001 | 0.006 |
| 5 | Homogeneous | 0.072 | 0.073 | 0.073 |
|   | Heterogeneous | 0.004 | 0.001 | 0.003 |

As clearly understood from the test results shown above, the test result through the analysis method relating to this invention is found very approximating to that through the chemical analysis method. Therefore, it may be said that said analysis method relating to this invention is an acceptably accurate technique.

Next, the test data of the measurement of the reproducibility are as follows:

|  | Standard deviation through conventional method (%) | Standard deviation through method relating to this invention (%) |
|---|---|---|
| Sample comprising 0.035% of homogeneous state of A | 0.0013 | 0.0007 |
| Sample comprising 0.005% of heterogeneous state of A | 0.0015 | 0.0006 |

The data shown above was obtained through each method of analysis by repetition of ten times respectively. Also, from the data, the high level of reproducibility of the analysis method relating to this invention is proved.

In said analysis method relating to this invention, discharging is repeated at the rate of 60 to 400 times/sec. In this case, the discharging shall be made continuously as long as approximately 10 seconds for 600 to 4,000 times, which eliminates the necessity of keeping the measurement until the intensity of emission has been stabilized as seen in the case of conventional analysis method.

Therefore, said analysis method relating to this invention not only allows the analysis to be made more speedily, but also can make the analysis with such an excellent reproducibility stabilized as being about two times of that of the conventional method.

The present invention may be embodied in other specific forms without departing from the spirit or essential characteristics thereof. The present disclosed embodiments are, therefore, to be considered in all respects as illustrative and not restrictive, the scope of the invention being indicated by the appended claims rather than the foregoing description, and all changes which come within the meaning and range of equivalency of the claims are, therefore, to be embraced therein.

What is claimed:

1. A method of emission spectrochemical analysis comprising:
   (a) producing a predetermined number of spark discharges between an electrode and a specimen containing an element in a first and second state;
   (b) measuring the intensity of emission of light caused by each of said spark discharges;
   (c) obtaining the frequency distribution of said measured intensities of emission;
   (d) separating in said distribution an area of normal distribution and an area outside said area of normal distribution;
   (e) selecting an intensity of emission value from said frequency distribution;
   (f) determining the amount of said element in said first state as a function of the selected intensity of emission value multiplied by the area of normal distribution; and
   (g) determining the amount of said element in said second state as a function of the selected intensity of emission value multiplied by the area outside the area of normal distribution.

2. The method of claim 1 wherein said area of the normal distribution is obtained by doubling the frequency between the starting point of said frequency distribution curve and the point at which the intensity of emission has the maximum frequency.

3. The method of claim 1 or 2 wherein the selected intensity of emission value is the median value of the frequency distribution of the measured intensity of emission.

4. The method of claim 1 or 2 wherein the selected intensity of emission value is the intensity at the maximum frequency in the frequency distribution of the measured intensity of emission.

* * * * *